US008158633B2

(12) United States Patent
Hendrix et al.

(10) Patent No.: US 8,158,633 B2
(45) Date of Patent: Apr. 17, 2012

(54) PHENYL-SUBSTITUTED PYRAZOLOPYRIMIDINES

(75) Inventors: Martin Hendrix, Odenthal (DE); Frank-Gerhard Böβ, Berkshire (GB); Nils Burkhardt, Velbert (DE); Christina Erb, Kriftel (DE); Adrian Tersteegen, Velbert (DE); Marja Van Kampen, Düsseldorf (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 585 days.

(21) Appl. No.: 10/525,115

(22) PCT Filed: Aug. 12, 2003

(86) PCT No.: PCT/EP03/08923
§ 371 (c)(1),
(2), (4) Date: Aug. 31, 2005

(87) PCT Pub. No.: WO2004/018474
PCT Pub. Date: Mar. 4, 2004

(65) Prior Publication Data
US 2006/0106035 A1    May 18, 2006

(30) Foreign Application Priority Data

Aug. 23, 2002   (DE) .................................. 102 38 723

(51) Int. Cl.
*A01N 43/90* (2006.01)
*A61K 31/519* (2006.01)
*C07D 487/00* (2006.01)
(52) U.S. Cl. ..................................... 514/262.1; 544/262
(58) Field of Classification Search .................... None
See application file for complete search history.

(56) References Cited

U.S. PATENT DOCUMENTS

| | | |
|---|---|---|
| 3,165,520 A | 1/1965 | Schmidt et al. |
| 3,169,965 A | 2/1965 | Schmidt et al. |
| 3,211,731 A | 10/1965 | Schmidt et al. |
| 3,732,225 A | 5/1973 | Breuer et al. |
| 5,002,949 A | 3/1991 | Peseckis |
| 5,041,449 A | 8/1991 | Belleau et al. |
| 5,047,407 A | 9/1991 | Belleau et al. |
| 5,053,499 A | 10/1991 | Kojima et al. |
| 5,256,668 A | 10/1993 | Hsu |
| 5,270,315 A | 12/1993 | Belleau et al. |
| 5,294,612 A | 3/1994 | Bacon et al. |
| 5,466,806 A | 11/1995 | Belleau et al. |
| 5,541,187 A | 7/1996 | Bacon et al. |
| 5,563,049 A | 10/1996 | Kojima et al. |
| 5,656,629 A | 8/1997 | Bacon |
| 5,684,164 A | 11/1997 | Belleau et al. |
| 5,750,673 A | 5/1998 | Martin |
| 5,948,812 A | 9/1999 | Kraft |
| 5,969,116 A | 10/1999 | Martin |
| 5,969,499 A | 10/1999 | Shaffer |
| 5,977,118 A | 11/1999 | Bacon |
| 5,977,332 A | 11/1999 | Martin |
| 6,100,037 A | 8/2000 | Phillips et al. |
| 6,174,884 B1 | 1/2001 | Haning et al. |
| 6,175,008 B1 | 1/2001 | Belleau et al. |
| 6,211,158 B1 | 4/2001 | Seela et al. |
| 6,225,315 B1 | 5/2001 | Ellis |
| 6,350,753 B1 | 2/2002 | Belleau et al. |
| 6,458,796 B1 | 10/2002 | Haning et al. |
| 6,479,463 B1 | 11/2002 | Wang et al. |
| 6,831,174 B2 | 12/2004 | Belleau et al. |
| 6,903,224 B2 | 6/2005 | Belleau et al. |
| 7,022,709 B2 | 4/2006 | Böess et al. |
| 7,067,507 B2 * | 6/2006 | Pulley et al. .................. 514/183 |
| 7,122,693 B2 | 10/2006 | Belleau et al. |
| 7,488,733 B2 | 2/2009 | Hendrix et al. |
| 7,615,558 B2 | 11/2009 | Hendrix et al. |
| 7,737,156 B2 | 6/2010 | Boss et al. |
| 2001/0041797 A1 | 11/2001 | Belleau et al. |
| 2001/0044441 A1 | 11/2001 | Campbell et al. |
| 2002/0016348 A1 | 2/2002 | Simitchieva et al. |
| 2002/0058663 A1 | 5/2002 | Varming et al. |
| 2002/0074774 A1 | 6/2002 | Hsu et al. |
| 2002/0086160 A1 | 7/2002 | Qiu et al. |
| 2002/0132754 A1 | 9/2002 | Boss et al. |
| 2003/0087918 A1 | 5/2003 | Belleau et al. |
| 2004/0185459 A1 | 9/2004 | Otsuka et al. |
| 2004/0220186 A1 | 11/2004 | Bell et al. |
| 2004/0254201 A1 | 12/2004 | Belleau et al. |
| 2004/0266736 A1 | 12/2004 | Wunder |
| 2005/0209251 A1 | 9/2005 | Linker et al. |
| 2006/0100222 A1 * | 5/2006 | Boss et al. ................. 514/262.1 |
| 2006/0106035 A1 | 5/2006 | Hendrix |

(Continued)

FOREIGN PATENT DOCUMENTS

CA                   1 311 201          12/1992

(Continued)

OTHER PUBLICATIONS

Accessed on Mar. 18, 2007. http://www.mentalhealth.org.uk/information/mental-health-a-z/dementia/.* Vippagunta et. al. Advanced Drug Delivery Reviews 48 (2001) 3-26.*
http://en.wikipedia.org/wiki/Amnesia, last accessed on Dec. 18, 2008.*
http://www.mentalhealth.org.uk/information/mental-health-a-z/dementia/, last accessed on Dec. 18, 2008.*
Miyashita, et. al., Heterocycles (1990), 31(7), 1309-14.*
http://www.nlm.nih.gov/medlineplus/ency/article/000746.htm, last accessed Jul. 15, 2010.*
Wei, et al., Molecular and Pharmacological Analysis of Cyclic Nucleotide-Gated Channel Function in the Central Nervous System, Progress in Neurobiology, vol. 56, 1998, pp. 37-64.
Fisher, et al., Isolation and Characterization of PDE9A, A Novel Human cGMP-specific Phosphodiesterase, Journal of Biological Chemistry, vol. 273, No. 25, 1998, pp. 15559-15564.
Guipponi, et al., Identification and Characterization of a Novel Cyclic Nucleotide Phosphodiesterase Gene (PDE9A) That Maps to 21q22.3: Alternative Splicing of mRNA Transcripts, Genomic Structure and Sequence, Hum Genet, vol. 103, 1998, pp. 386-392.
Sonderling, et al., Identification and Characterization of a Novel Family of Cyclic Nucleotide Phosphodiesterases, Journal of Biological Chemistry, vol. 273, No. 25, pp. 15553-15558.
Andreeva, et al., Expression of cGMP-Specific Phosphodiesterase 9A mRNA in the Rat Brain, Journal of Neuroscience, vol. 21, No. 22, 2001, pp. 9068-9076.

(Continued)

*Primary Examiner* — Jeffrey Murray
(74) *Attorney, Agent, or Firm* — Michael P. Morris; Edward S. Lazer

(57) ABSTRACT

The invention relates to novel phenyl-substituted pyrazolopyrimidines, process for their preparation, and their use for producing medicaments for improving perception, concentration, learning and/or memory.

10 Claims, No Drawings

U.S. PATENT DOCUMENTS

| | | |
|---|---|---|
| 2006/0111372 A1 | 5/2006 | Hendrix |
| 2007/0037977 A1 | 2/2007 | Belleau et al. |
| 2007/0105876 A1 | 5/2007 | Hendrix |
| 2007/0105881 A1 | 5/2007 | Hendrix et al. |
| 2007/0161662 A1 | 7/2007 | Hendrix |
| 2008/0255118 A1 | 10/2008 | Hendrix et al. |
| 2009/0111838 A1 | 4/2009 | Hendrix et al. |
| 2009/0121919 A1 | 5/2009 | Kihara et al. |
| 2010/0035900 A1 | 2/2010 | Hendrix et al. |
| 2010/0210839 A1 | 8/2010 | Boess et al. |
| 2011/0015193 A1 | 1/2011 | Eickmeier et al. |
| 2011/0065730 A1 | 3/2011 | Hendrix et al. |
| 2011/0082137 A1 | 4/2011 | Giovannini et al. |

FOREIGN PATENT DOCUMENTS

| | | |
|---|---|---|
| CA | 2 283 211 | 9/1998 |
| CA | 2 238 211 | 12/1998 |
| CA | 2 357 146 | 7/2000 |
| CA | 2 438 890 | 9/2002 |
| CA | 2 417 631 | 1/2003 |
| CA | 2 466 824 | 5/2003 |
| CA | 2 484 997 | 11/2003 |
| CA | 2 496 194 | 3/2004 |
| CA | 2 496 292 | 4/2004 |
| CA | 2 496 308 | 4/2004 |
| CA | 2 524 900 | 11/2004 |
| CH | 396 923 | 8/1965 |
| CH | 396924 | 8/1965 |
| CH | 396925 | 8/1965 |
| CH | 396926 | 8/1965 |
| CH | 396927 | 8/1965 |
| CH | 398 626 | 3/1966 |
| DE | 1147234 | 4/1963 |
| DE | 1149013 | 5/1963 |
| DE | 1 153 023 | 8/1963 |
| DE | 1 156 415 | 10/1963 |
| DE | 2408906 | 2/1974 |
| DE | 4 004 558 | 9/1990 |
| DE | 101 56 249 | 5/2003 |
| DE | 102 38 722 | 3/2004 |
| EP | 0 130 735 | 1/1985 |
| EP | 0 286 028 | 10/1988 |
| EP | 0 496 617 | 7/1992 |
| EP | 0 626 387 | 11/1994 |
| EP | 0 679 657 | 11/1995 |
| EP | 0 995 751 | 4/2000 |
| EP | 1 460 077 | 9/2004 |
| GB | 937 723 | 9/1963 |
| GB | 937 724 | 9/1963 |
| GB | 937724 * | 9/1963 |
| GB | 937726 | 9/1963 |
| GB | 973361 | 10/1964 |
| JP | 11-501923 | 2/1999 |
| JP | 2001 514638 | 9/2001 |
| JP | 2002 523507 | 7/2002 |
| JP | 2004 536933 | 12/2004 |
| JP | 2005 531549 | 10/2005 |
| JP | 2006 501272 | 1/2006 |
| JP | 2006 503051 | 1/2006 |
| WO | WO-94 14802 | 7/1994 |
| WO | WO-94 17803 | 8/1994 |
| WO | WO 95/10506 | 4/1995 |
| WO | WO-96 28429 | 9/1996 |
| WO | WO-97 16456 | 5/1997 |
| WO | WO-97 46569 | 12/1997 |
| WO | WO-98 00434 | 1/1998 |
| WO | WO 98/10765 | 3/1998 |
| WO | WO-98 16184 | 4/1998 |
| WO | 9840384 | 9/1998 |
| WO | WO 99/41253 | 8/1999 |
| WO | WO 00/18758 | 4/2000 |
| WO | WO-00 43394 | 7/2000 |
| WO | WO-01 60315 | 8/2001 |
| WO | WO-01 77075 | 10/2001 |
| WO | WO 02/06288 | 1/2002 |
| WO | WO-02 09713 | 2/2002 |
| WO | WO-02 16348 | 2/2002 |
| WO | WO 02/055082 | 7/2002 |
| WO | WO-02 057425 | 7/2002 |
| WO | WO-02 074774 | 9/2002 |
| WO | WO-02 086160 | 10/2002 |
| WO | WO 02/098864 | 12/2002 |
| WO | WO-03 011925 | 2/2003 |
| WO | WO-03 022859 | 3/2003 |
| WO | WO-03 037432 | 5/2003 |
| WO | WO 03/037899 | 5/2003 |
| WO | WO-03 041725 | 5/2003 |
| WO | WO-03 072757 | 9/2003 |
| WO | WO 03/093269 | 11/2003 |
| WO | WO-03 099840 | 12/2003 |
| WO | WO-2004 002999 | 1/2004 |
| WO | WO-2004 018474 | 3/2004 |
| WO | WO-2004 026286 | 4/2004 |
| WO | WO-2004 026876 | 4/2004 |
| WO | WO-2004 046331 | 6/2004 |
| WO | WO-2004 096811 | 11/2004 |
| WO | WO-2004 099210 | 11/2004 |
| WO | WO-2004 099211 | 11/2004 |
| WO | WO-2004 108139 | 12/2004 |
| WO | WO-2004 113306 | 12/2004 |
| WO | WO-01 05758 | 1/2005 |
| WO | WO-2005 051944 | 6/2005 |
| WO | WO-2005 068436 | 7/2005 |
| WO | WO-2006 076455 | 7/2006 |
| WO | WO-2006 084281 | 8/2006 |
| WO | WO-2006 091095 | 8/2006 |
| WO | WO-2006 125548 | 11/2006 |
| WO | WO-2007 025043 | 3/2007 |
| WO | WO-2007 046747 | 4/2007 |
| WO | WO-2008 005542 | 1/2008 |
| WO | WO-2008 010047 | 1/2008 |
| WO | WO-2008 055959 | 5/2008 |
| WO | WO-2008 100447 | 8/2008 |
| WO | WO-2008 104077 | 9/2008 |
| WO | WO-2008 139293 | 11/2008 |
| WO | WO-2009 068617 | 6/2009 |
| WO | WO-2009 121919 | 10/2009 |
| WO | WO-2010 026214 | 3/2010 |
| WO | WO-2010 112437 | 10/2010 |
| WO | WO-2011 018495 | 2/2011 |

OTHER PUBLICATIONS

Martins, et al., Purification and Characterization of a Cyclic GMP-stimulated Cyclic Nucleotide Phosphodiesterase from Bovine Tissues, Journal of Biological Chemistry, vol. 257, No. 4, 1982, pp. 1973-1979.

Francis, et al. Characterization of a Novel cGMP Binding Protein from Rat Lung, Journal of Biological Chemistry, vol. 255, No. 2, 1980, pp. 620-626.

Gillespie, et al., Characterization of a Bovine Cone Photoreceptor Phosphodiesterase Purified by Cyclic GMP-Sepharose Chromatography, Journal of Biological Chemistry, vol. 263, No. 17, 1988, pp. 8133-8141.

Fawcett, et al., Molecular Cloning and Characterization of a Distinct Human Phosphodiesterase Gene Family: PDE11A, Proc. Natl. Acad. Sci., vol. 97, No. 7, 2000, pp. 3702-3707.

Murashima, et al., Characterization of Particulate Cyclic Nucleotide Phosphodiesterases from Bovine Brain: Purification of a Distinct cGMP-Stimulated Isoenzyme, Biochemistry, vol. 29, No. 22, 1990, pp. 5285-5292.

Van Der Staay, J. et al., "The Novel selective PDE9 inhibitor BAY 73-6691 improves learning and memory in rodents," Neuropharmacology, 2008, vol. 55, pp. 908-918.

Francis, P. T., "Glutamatergic systems in Alzheimer's Disease," International Journal of the Geriatric Psychiatry, 2003, vol. 18, pp. S15-S21.

Francis, P. T. et al., "Cortical Pyramidal Neurone Loss May Cause Glutamatergic Hypoactivity and Cognitive Impairment in Alzheimer's Disease: Investigative and Therapeutic Perspectives," Journal of Neurochemistry, 1993.

Puzzo, D. et al., "Amyloid-Beta Peptide Inhibits Activation of the Nitric Oxide/cGMP/cAMP-Responsive Element-Binding Protein Pathway during Hippocampal Synaptic Plasticity" Neurobiology of Disease, Jul. 20, 2005, vol. 25, No. 29, pp. 6887-6897.

Reymann, K. G. et al., "The late maintenance of hippocampal LTP: Requirements, phases, 'synaptic tagging', 'late associativity' and the implications," Neuropharmacology, 2007, vol. 52, pp. 24-40.

Wang, H et al., "Insight into Binding of Phosphodiesterase-9A Selective Inhibitors by Crystal Structures and Mutagenesis," Journal of Medicinal Chemistry, Oct. 12, 2009.

Deninno, M. P. et al., "The discovery of potent, selective, and orally bioavailable PDE9 inhibitors as potential hypoglycemic agents," Bioorganic & Medicinal Chemistry Letters, 2009, vol. 19, pp. 2537-2541.

Hendrix et al., "Use of Pyrazolopyrimidine Against Cardiovascular Disease," Publication Date: Nov. 30, 2006, Data Supplied from the espacenet database Worldwide; English Abstract of WO 2006125548.

Hendrix et al., "6-cyclymethyl- and 6-alkylmethyl-Substituted Pyrazolopyrimidines," Publication Date: Nov. 18, 2004, Data Supplied from the espacenet database Worldwide; English Abstract of WO 2004099211.

Barger et al., "Role of cyclic GMP in the Regulation of Neuronal Calcium and Survival by Secreted Forms of Beta-Amyloid Precursor," J of Neurochem, 1995, vol. 64, No. 5, pp. 2087-2096.

Byrn et al., Solid State Chemistry of Drugs, 1999, vol. 2, No. 10, pp. 232-247.

Chem Abstracts Service, Database Accession No. ALB-H01677136, Database Chemcats, 2007, XP002556399.

Cheng et al., "Potential Purine Antagonists VII. Synthesis of 6-Alkylpyrazolo-[3,4-d]pyrimidines" Potential Purine Antagonist VII, 1958, vol. 23, pp. 191-200.

Doerwald et al., "Side reactions in organic synthesis," A Guide to Successful Synthesis Design, 2005, 4 pages.

Ebert et al., "Scopolamine model of demential: electroencephalogram findings and cognitive performance," Europ J of Clinical Investigation, 1998, vol. 28, No. 11, pp. 944-949.

Harb et al., "Pyrazoles as building blocks in heterocyclic synthesis..," Chemical Papers, 2005, vol. 59, No. 3, pp. 187-159, XP002498868.

Hung et al., "A high-yielding synthesis of monalkylhydrazines," Journal of Organic Chemistry, 1981, vol. 46, pp. 5413-5414.

International Search Report for PCT/EP2004/006477 dated Oct. 27, 2004.

International Search Report for PCT/EP2004/014872 dated May 19, 2005.

International Search Report of PCT/EP2003/08880 dated Apr. 16, 2004.

International Search Report of PCT/EP2003/08923 dated Dec. 15, 2003.

International Search Report of PCT/EP2003/08979 dated Nov. 25, 2003.

International Search Report of PCT/EP2004/004412 dated Jul. 14, 2004.

International Search Report of PCT/EP2004/004455 dated Sep. 17, 2004.

Markwalder, J. A. et al., "Synthesis and Biological Evaluation of 1-Aryl-4,5-dihydro-1H-pyrazolo[3.4-d]pyrimidin-4-one Inhibitors of Cyclin-Dependent Kinases," J of Med Chemistry, 2004, vol. 47, pp. 5894-5911, XP002399637.

Podraza et al., "Reductive Cyclization of Ketoesters Utilizing Sodium Cyanoborohydride: Synthesis of γ- and δ-lactones," J of Heterocyclic Chem., 1987, vol. 24, pp. 293.

Prickaerts et al., "Effects of two selective phosphodiesterase type 5 inhibitors, sildenafil and vardenafil, on object recognition memory and hippocampal cyclic gmp levels in the rat," Neuroscience, 2002, vol. 113, pp. 351-361.

Prickaerts et al., "Possible role of nitric oxide-cyclic GMP pathway in object recognition memory: Effects of 7 nitroindazole and zaprinast," Europ J of Pharmacology, 1997, vol. 337, No. 2-3, pp. 125-136.

Reid et al., Current Pharmaceutical Design, 1999, vol. 5, No. 9, pp. 725-735.

Schmidt et al., "Pyrazolo[3, 4-d] pyrimidin-nucleoside," Chemische Berichte, 1977, vol. 110, pp. 2445-2455.

Skipper et al., "Structure-Activity Relationships Observed on Screening a Series of Pyrazolopyrimidines against Experimental Neoplasms," Cancer Research, 1957, vol. 17, pp. 579-596.

Timberlake et al., "Chemistry of Hydrazo-, Azo-, and Azoxy Groups," Patai, 1975, Chapter 4.

Ugarkar et al., "Synthesis and antiviral/antitumor activities of . . . ," Journal of Medicinal Chemistry, 1984, vol. 27, No. 8, pp. 1026-1030.

Ulrich et al., "Crystallization," Kirk-Othmer Encyclopedia of Chem. Techn., 2002, 7 pages.

Van Staveren et al., "Cloning and localization of the cGMP-specific phosphodiesterase type 9 in the rat brain," Journal of Neurocytology, 2002, vol. 31, pp. 729-741.

Wang et al., "Identification and characterization of a new human type 9 cGMP-specific phosphodiesterase-splice variant (PDE9A5) Different tissue distribution and subcellular localization of PDE9A variants," Gene, 2003, vol. 314, pp. 15-27.

Weeber et al., "Molecular genetics of human cognition," Molecular Interventions, 2002, vol. 2, No. 6, pp. 376-391.

West et al., "Solid Solutions," Dept of Chem Univ of Aberdeen, 1988, vol. 18, 3 pages.

Ciba Geigy Ag, "Nucleosides and oligonucleotides and 2'-ether groups," Data Supplied from the espacenet database, Publication Date: Nov. 30, 1994; English Abstract of EP0 626 387.

Thomson Innovation Record View, Publication Date: Aug. 15, 1965; English Abstract of CH 396 923.

Related U.S. Appl. No. 13/099,064, filed May 2, 2011.
Related U.S. Appl. No. 12/935,686, filed Sep. 30, 2010.
Related U.S. Appl. No. 13/062,625, filed Mar. 7, 2011.
Related U.S. Appl. No. 12/855,129, filed Aug. 12, 2010.

International Search Report for PCT/EP2010/061735 dated Sep. 24, 2010.

International Search Report for PCT/EP2010/054050 dated May 27, 2010.

International Preliminary Report on Patentability for PCT/EP2009/061455 dated Mar. 17, 2011.

International Search Report for PCT/EP2009/061455 dated Feb. 19, 2010.

International Preliminary Report on Patentability for PCT/EP2009/053907 dated Oct. 14, 2010.

International Search Report for PCT/EP2008/066350 dated Feb. 23, 2009.

International Search Report for PCT/EP2009/053907 dated May 26, 2009.

Accessed on Jun. 30, 2008, Intelihealth: "Alzheimer's disease," http://www.intelihealth.com/IH/iht1 H/WSIHW000/8303/9117/195703.html?d=dmtHealthAZ.

Accessed on Sep. 22, 2009: Intelihealth: "Dementia", http://www.intelihealth.com/IH/ihtIH/WSIHW000/244798/00084.html.

Accessed on Sep. 22, 2009: Intelihealth: "Parkinson's Disease", http://www.intelihealth.com/IH/ihtlH?d=dmtHealthAZ&c=201957.

Bernabeu, R. et al., "Hippocampal cGMP and cAMP are differentially involved in memory processing of inhibitory avoidance learning," Neuroreport, 1996, vol. 7, No. 2, pp. 585-588.

Farlow, M. R., "Pharmacokinetic profiles of current therapies for Alzheimer's Disease: Implications for Switching to Galantamine," Clinical Therapeutics, 2001, vol. 23, pp. A13-A24.

Soderling, et al., Regulation of cAMP and cGMP signaling: new phosphodiesterases and new functions, Current Opinion in Cell Biology, vol. 12, 2000, pp. 174-179.

Miyashita, et al., Studies on Pyrazolo[3,4-d]Pyrimidine Derivatives. XVIII. Facile Preparation of 1H-Pyrazolo[3,4-d]Pyrimidin-4(5H)-Ones, Heterocycles, vol. 31, No. 7, 1990, p. 1309-1314.

Schmidt, et al., Heilmittelchemische Studien in der Heterocyclischen Reihe 34. Mitteilung[1]) Pyrazolo-pyrimidine V[2]) Eine neue Synthese von Pyrazolo[3,4-d]Pyrimidinen mit coronarerweiternden Eigenschaften, Helvetica Chimica Acta, No. 189, 1962, pp. 1620-1627.

Loughney, et al., Isolation and Characterization of cDNAs Corresponding to Two Human Calcium, Calmodulin-regulated, 3',5'-Cyclic Nucleotide Phosphodiesterases, Journal of Biological Chemistry, vol. 271, No. 2, 1996, pp. 796-806.

Rosman, et al., Isolation and Characterization of Human cDNAs encoding a cGMP-stimulated 3',5'-Cyclic Nucleotide Phosphodiesterase, Gene, vol. 191, 1997, pp. 89-95.

Miki, et al., Characterization of the cDNA and Gene Encoding Human PDE3B, the cGIP1 Isoform of the Human Cyclic GMP-Inhibited Cyclic Nucleotide Phosphodiesterase Family, Genomics, vol. 36, 1996, pp. 476-485.

Obernolte, et al., The cDNA of a Human Lymphocyte cyclic-AMP Phosphodiesterase (PDE IV) Reveals a Multigene Family, Gene, vol. 129, 1993 pp. 239-247.

Loughney, et al., Isolation and Characterization of cDNAs encoding PDE5A, a Human cGMP-Binding, cGMP-Specific 3',5'-Cyclic Nucleotide Phosphodiesterase, Gene, vol. 216, 1998, pp. 139-147.

Hetman, et al., Cloning and Characterization of PDE7B, a cAMP-specific Phosphodiesterase, Proc. Natl. Acad. Sci., vol. 97, No. 1, 2000, pp. 472-476.

Fisher, et al., Isolation and Characterization of PDE8A, a Novel Human cAMP-Specific Phosphodiesterase, Biochemical and Biophysical Research Communications, vol. 246, 1998, pp. 570-577.

Fujishige, et al., Cloning and Characterization of a Novel Human Phosphodiesterase That Hydrolyzes Both cAMP and cGMP (PDE10A), Journal of Biological Chemistry, vol. 274, No. 26, 1999, pp. 18438-18445.

Huettner, et al., Primary Culture of Identified Neurons from the Visual Cortex of Postnatal Rats, Journal of Neuroscience, vol. 6, 1986, pp. 3044-3060.

Frank Wunder, et al; Characterization of the First Potent and Selective PDE9 Inhibitor Using a cGMP Reporter Cell Line; Molecular Pharmacology (2005) vol. 68, No. 6 pp. 1775-1781.

Magnus Roenn, et al; Palladium (II)-Catalyzed Cyclization Using Molecular Oxygen as Reoxidant; Tetrahedron Letters (1995) vol. 36, No. 42, pp. 7749-7752.

Hieke Gielen, et al; A Novel Approach to Amidines from Esters; Tetrahedron Letters (2002) vol. 43 pp. 419-421.

K. Hemender Reddy, et al; Versatile Synthesis of 6-Alkyl/Aryl-1H-1-Pyrazolo[3,4-d]Pyrimidin-4[5H]-Ones; Indian Journal of Chemistry (1992) vol. 31B, pp. 163-166.

Arne Schousboe, et al; Role of Ca++ and Other Second Messengers in Excitatory Amino Acid Receptor Mediated Neuogeneration: Clinical Perspective; Clinical Neuroscience (1997) vol. 4, pp. 194-198.

Claire Lugnier; Cyclic Nucleotide Phosphodiesterase (PDE) Superfamily: A New Target for the Development of Specific Therapeutic Agents; Pharmacology & Therapeutics (2006) vol. 109 pp. 366-398.

Jehan Bagli, et al; Chemistry and Positive Inotropic Effect of Pelrinone and related Derivates. A Novel Class of 2-Methylpyrimidones as Inotropic Agents; Journal of Medicinal Chemistry (1988) vol. 31 pp. 814-823.

Rudolf Gompper, et al; Substituted Dithiocarboxylic Acids and Ketene Thioacetals; Institute for Organic Chemistry Technology (1962) vol. 95, pp. 2861-2870. German & English Translation.

* cited by examiner

PHENYL-SUBSTITUTED PYRAZOLOPYRIMIDINES

This application is a 371 of PCT/EP2003/008923, filed Aug. 12, 2003.

The invention relates to novel phenyl-substituted pyrazolopyrimidines, process for their preparation, and their use for producing medicaments for improving perception, concentration, learning and/or memory.

Cellular activation of adenylate cyclases and guanylate cyclases brings about the cyclization of respectively ATP and GTP to 5'-3' cyclic adenosine monophosphate (cAMP) and 5'-3' cyclic guanosine monophosphate (cGMP). These cyclic nucleotides (cAMP and cGMP) are important second messengers and therefore play a central role in cellular signal transduction cascades. Each of them reactivates inter alia, but not exclusively, protein kinases. The protein kinase activated by cAMP is called protein kinase A (PKA), and the protein kinase activated by cGMP is called protein kinase G (PKG). Activated PKA and PKG are able in turn to phosphorylate a number of cellular effector proteins (e.g. ion channels, G-protein-coupled receptors, structural proteins). It is possible in this way for the second messengers cAMP and cGMP to control a wide variety of physiological processes in a wide variety of organs. However, the cyclic nucleotides are also able to act directly on effector molecules. Thus, it is known, for example, that cGMP is able to act directly on ion channels and thus is able to influence the cellular ion concentration (review in: Wei et al., *Prog. Neurobiol.*, 1998, 56: 37-64). The phosphodiesterases (PDE) are a control mechanism for controlling the activity of cAMP and cGMP and thus in turn these physiological processes. PDEs hydrolyze the cyclic monophosphates to the inactive monophosphates AMP and GMP. At least 21 PDE genes have now been described (*Exp. Opin. Investig. Drugs* 2000, 9, 1354-3784). These 21 PDE genes can be divided on the basis of their sequence homology into 11 PDE families (for proposed nomenclature, see http://depts.washington.edu/pde/Nomenclature.html.). Individual PDE genes within a family are differentiated by letters (e.g. PDE1A and PDE1B). If different splice variants within a gene also occur, this is then indicated by an additional numbering after the letter (e.g. PDE1A1).

Human PDE9A was cloned and sequenced in 1998. The amino acid identity with other PDEs does not exceed 34% (PDE8A) and is never less than 28% (PDE5A). With a Michaelis-Menten constant (Km) of 170 nM, PDE9A has high affinity for cGMP. In addition, PDE9A is selective for cGMP (Km for cAMP=230 µM). PDE9A has no cGMP binding domain, suggesting allosteric enzyme regulation by cGMP. It was shown in a Western blot analysis that PDE9A is expressed in humans inter alia in testes, brain, small intestine, skeletal muscle, heart, lung, thymus and spleen. The highest expression was found in the brain, small intestine, heart and spleen (Fisher et al., *J. Biol. Chem.*, 1998, 273 (25): 15559-15564). The gene for human PDE9A is located on chromosome 21q22.3 and comprises 21 exons. To date, 4 alternative splice variants of PDE9A have been identified (Guipponi et al., *Hum. Genet.*, 1998, 103: 386-392). Classical PDE inhibitors do not inhibit human PDE9A. Thus, IBMX, dipyridamole, SKF94120, rolipram and vinpocetine show no inhibition on the isolated enzyme in concentrations of up to 100 µM. An $IC_{50}$ of 35 µM has been demonstrated for zaprinast (Fisher et al., *J. Biol. Chem.*, 1998, 273 (25): 15559-15564).

Murine PDE9A was cloned and sequenced in 1998 by Soderling et al. (*J. Biol. Chem.*, 1998, 273 (19): 15553-15558). This has, like the human form, high affinity for cGMP with a Km of 70 nM. Particularly high expression was found in the mouse kidney, brain, lung and heart. Murine PDE9A is not inhibited by IBMX in concentrations below 200 µM either; the $IC_{50}$ for zaprinast is 29 µM (Soderling et al., *J. Biol. Chem.*, 1998, 273 (19): 15553-15558). It has been found that PDE9A is strongly expressed in some regions of the rat brain. These include olfactory bulb, hippocampus, cortex, basal ganglia and basal forebrain (Andreeva et al., *J. Neurosci.*, 2001, 21 (22): 9068-9076). The hippocampus, cortex and basal forebrain in particular play an important role in learning and memory processes.

As already mentioned above, PDE9A is distinguished by having particularly high affinity for cGMP. PDE9A is therefore active even at low physiological concentrations, in contrast to PDE2A (Km=10 µM; Martins et al., *J. Biol. Chem.*, 1982, 257: 1973-1979), PDE5A (Km=4 µM; Francis et al., *J. Biol. Chem.*, 1980, 255: 620-626), PDE6A (Km=17 µM; Gillespie and Beavo, *J. Biol. Chem.*, 1988, 263 (17): 8133-8141) and PDE11A (Km=0.52 µM; Fawcett et al., *Proc. Nat. Acad. Sci.*, 2000, 97 (7): 3702-3707). In contrast to PDE2A (Murashima et al., *Biochemistry*, 1990, 29: 5285-5292), the catalytic activity of PDE9A is not increased by cGMP because it has no GAF domain (cGMP-binding domain via which the PDE activity is allosterically increased) (Beavo et al., *Current Opinion in Cell Biology*, 2000, 12: 174-179). PDE9A inhibitors may therefore lead to an increase in the baseline cGMP concentration. This increase in the baseline cGMP concentration surprisingly led to an improvement in learning and memory in the social recognition test.

WO 98/40384 discloses pyrazolopyrimidines which are PDE1, 2 and 5 inhibitors and can be employed for the treatment of cardiovascular and cerebrovascular disorders and disorders of the urogenital system.

CH 396 924, CH 396 925, CH 396 926, CH 396 927, DE 1 147 234, DE 1 149 013, GB 937,726 describe pyrazolopyrimidines which have a coronary-dilating effect and which can be employed for the treatment of disturbances of myocardial blood flow.

U.S. Pat. No. 3,732,225 describes pyrazolopyrimidines which have an antiinflammatory and blood glucose-lowering effect.

DE 2 408 906 describes styrenepyrazolopyrimidines which can be employed as anti-microbial and antiinflammatory agents for the treatment of, for example, edema.

The present invention relates to compounds of the formula

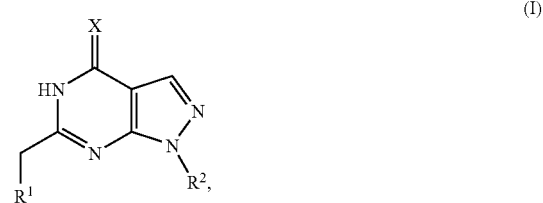

(I)

in which $R^1$ is phenyl which is substituted by 1 to 5 substituents independently of one another selected from the group of halogen, $C_1$-$C_6$-alkyl, trifluoromethyl, trifluoromethoxy, cyano, hydroxy, nitro and $C_1$-$C_6$-alkoxy, $R^2$ is pentan-3-yl, $C_4$-$C_6$-cycloalkyl, X is oxygen or sulfur, and the salts, solvates and/or solvates of the salts thereof.

Compounds of the invention are the compounds of the formula (I) and the salts, solvates and solvates of the salts thereof; the compounds which are encompassed by formula (I) and have the formulae mentioned hereinafter and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Salts which are preferred for the purposes of the invention are physiologically acceptable salts of the compounds of the invention.

Physiologically acceptable salts of the compounds (I) include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Physiologically acceptable salts of the compounds (I) also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dehydroabietylamine, arginine, lysine, ethylenediamine and methylpiperidine.

Solvates refers for the purposes of the invention to those forms of the compounds which form, in the solid or liquid state, a complex by coordination with solvent molecules. Hydrates are a specific form of solvates in which the coordination takes place with water.

In addition, the present invention also encompasses prodrugs of the compounds of the invention. The term "prodrugs" encompasses compounds which themselves may be biologically active or inactive but are converted (for example by metabolism or hydrolysis) into compounds of the invention during their residence time in the body.

For the purposes of the present invention, the substituents have the following meaning, unless specified otherwise:

$C_1$-$C_6$-Alkoxy is a straight-chain or branched alkoxy radical having 1 to 6, preferably 1 to 4, particularly preferably having 1 to 3 carbon atoms. Preferred examples are methoxy, ethoxy, n-propoxy, isopropoxy, tert-butoxy, n-pentoxy and n-hexoxy.

$C_1$-$C_6$-Alkyl is a straight-chain or branched alkyl radical having 1 to 6, preferably 1 to 4, particularly preferably 1 to 3, carbon atoms. Preferred examples are methyl, ethyl, n-propyl, isopropyl, tert-butyl, n-pentyl and n-hexyl.

$C_4$-$C_6$- and $C_5$-$C_6$Cycloalkl are saturated or partially unsaturated cycloalkyl radicals having 4 to 6, preferably 5 to 6, carbon atoms. Preferred examples are cyclobutyl, cyclopentyl and cyclohexyl.

Halogen is for fluorine, chlorine, bromine and iodine. Fluorine, chlorine, bromine are preferred, and fluorine and chlorine are particularly preferred.

When radicals in the compounds of the invention are optionally substituted, unless otherwise specified substitution by up to three identical or different substituents is preferred.

The compounds of the invention may also be in the form of tautomers as shown by way of example below:

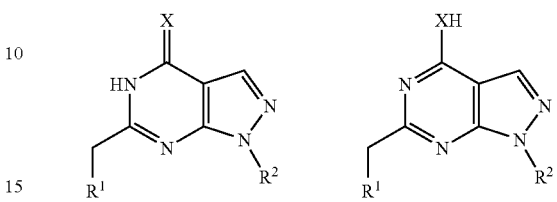

A further embodiment of the invention relates to compounds of the formula (I), in which $R^1$ is phenyl which is substituted by 1 to 3 substituents independently of one another selected from the group of fluorine, chlorine, bromine, $C_1$-$C_4$-alkyl, trifluoromethyl, trifluoromethoxy, cyano, hydroxy, nitro and $C_1$-$C_4$-alkoxy, $R^2$ is pentan-3-yl, $C_5$-$C_6$-cycloalkyl, X is oxygen or sulfur, and the salts, solvates and/or solvates of the salts thereof.

A further embodiment of the invention relates to compounds of the formula

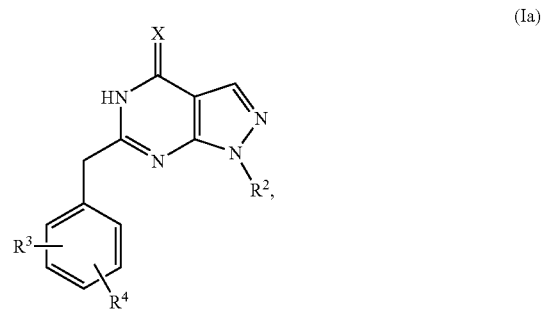

(Ia)

in which $R^3$ is hydrogen or chlorine, $R^4$ is fluorine, chlorine, bromine, methyl, trifluoromethyl, $R^2$ is pentan-3-yl, cyclopentyl, X is oxygen or sulfur, and the salts, solvates and or solvates of the salts thereof.

A further embodiment of the invention relates to compounds of the formulae (I) and (Ia), in which $R^3$ is hydrogen or chlorine, $R^4$ is fluorine, chlorine, bromine, methyl, trifluoromethyl, $R^2$ is pentan-3-yl, cyclopentyl, X is oxygen, and the salts, solvates and/or solvates of the salts thereof.

A process for preparing the compounds of the invention has additionally been found, characterized in that either

[A] compounds of the formula

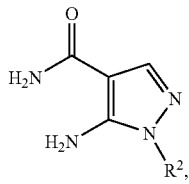
(II)

in which
R² has the meanings indicated above,
are converted by reaction with a compound of the formula R¹—CH₂—C(O)—Z  (IIIa), in which
R¹ has the meanings indicated above,
and
Z is chlorine or bromine,
in an inert solvent and in the presence of a base initially into compounds of the formula

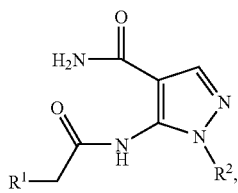
(IV)

in which
R¹ and R² have the meanings indicated above,
then cyclized in an inert solvent in the presence of a base to compounds of the formula

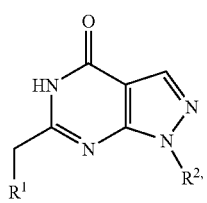
(Ib)

in which
R¹ and R² have the meanings indicated above,
or
[B] compounds of the formula (II) are reacted with direct cyclization to (Ib) with a compound of the formula R¹—CH₂—C(O)—OR⁵  (IIIb), in which
R¹ has the meanings indicated above,
and
R⁵ is methyl or ethyl,
in an inert solvent and in the presence of a base,
or

[C] compounds of the formula

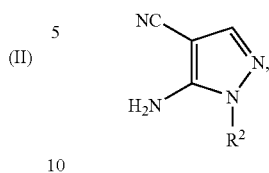
(V)

in which
R² has the meanings indicated above,
are converted initially by reaction with a compound of the formula (IIIa) in an inert solvent and in the presence of a base into compounds of the formula

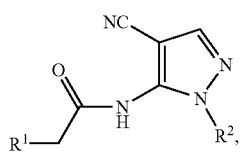
(VI)

in which
R¹ and R² have the meanings indicated above,
and the latter are cyclized in a second step in an inert solvent and in the presence of a base and of an oxidizing agent to (Ib),
and the compounds of the formula (Ib) are then converted where appropriate by reaction with a sulfurizing agent such as, for example, diphosphorus pentasulfide into the thiono derivatives of the formula

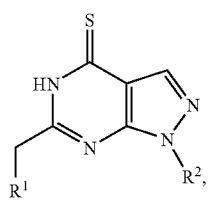
(Ic)

in which
R¹ and R² have the meanings indicated above,
and the resulting compounds of the formula (I) are reacted where appropriate with the appropriate (i) solvents and/or (ii) bases or acids to give the solvates, salts and/or solvates of the salts thereof.

Suitable for the first step of process [A] and of process [C] are inert organic solvents which are not changed under the reaction conditions. These preferably include ethers such as, for example, diethyl ether, dioxane, tetrahydrofuran or glycol dimethyl ether, or toluene or pyridine. It is likewise possible to employ mixtures of the solvents mentioned. Tetrahydrofuran, toluene or pyridine are particularly preferred.

Suitable bases are in general alkali metal hydrides such as, for example, sodium hydride, or cyclic amines such as, for example, piperidine, pyridine, dimethylaminopyridine (DMAP), or $C_1$-$C_4$-alkylamines such as, for example, triethylamine. Sodium hydride, pyridine and/or dimethylaminopyridine are preferred.

The base is generally employed in an amount of from 1 mol to 4 mol, preferably from 1.2 mol to 3 mol, in each case based on 1 mol of the compounds of the formula (II) or (V).

In a variant, the reaction is carried out in pyridine, to which a catalytic amount of DMAP is added. It is also possible where appropriate to add toluene.

The reaction temperature can generally be varied within a relatively wide range. It is generally in a range from −20° C. to +200° C., preferably from 0° C. to +100° C.

Solvents suitable for the cyclization in the second step of processes [A] and [C] are the usual organic solvents. These preferably include alcohols such as methanol, ethanol, propanol, isopropanol, n-butanol or tert-butanol, or ethers such as tetrahydrofuran or dioxane, or dimethylformamide or dimethyl sulfoxide. Alcohols such as methanol, ethanol, propanol, isopropanol or tert-butanol are particularly preferably used. It is likewise possible to employ mixtures of the solvents mentioned.

Bases suitable for the cyclization in the second step of processes [A] and [C] are the usual inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium bicarbonate, or alkali metal alcoholates such as sodium methanolate, sodium ethanolate, potassium methanolate, potassium ethanolate or potassium tert-butanolate. Potassium carbonate, sodium hydroxide and potassium tert-butanolate are particularly preferred.

The base for carrying out the cyclization is generally employed in an amount of from 2 mol to 6 mol, preferably from 3 mol to 5 mol, in each case based on 1 mol of the compounds of the formula (IV) or (VI).

Oxidizing agents suitable for the cyclization in the second step of process [C] are, for example, hydrogen peroxide or sodium borate. Hydrogen peroxide is preferred.

The cyclization in processes [A], [B] and [C] is generally carried out in a temperature range from 0° C. to +160° C., preferably at the boiling point of the particular solvent.

The cyclization is generally carried out under atmosphere pressure. It is, however, also possible to carry out the process under elevated pressure or reduced pressure (e.g. in a range from 0.5 to 5 bar).

Solvents suitable for process [B] are the alcohols listed above for the second step of processes [A] and [C], with preference for ethanol.

Bases suitable for process [B] are alkali metal hydrides such as, for example, sodium or potassium hydride, or alkali metal alcoholates such as, for example, sodium methanolate, ethanolate, isopropoxide or potassium tert-butoxide. Sodium hydride is preferred.

The base is employed in an amount of from 2 mol to 8 mol, preferably from 3 mol to 6 mol, in each case based on 1 mol of the compounds of the formula (II).

The compounds of the formula (II) are known or can be prepared for example by firstly condensing ethoxymethylenemalononitrile with hydrazine derivatives of the formula $$R^2\text{—NH—NH}_2 \quad (VII),$$

in which
R² has the meanings indicated above,
in an inert solvent to give the pyrazolenitriles of the formula (V), and then reacting the latter with one of the oxidizing agents listed above, preferably hydrogen peroxide, in the presence of ammonia [cf. for example, A. Miyashita et al., Heterocycles 1990, 31, 1309ff].

The compounds of the formulae (IIIa), (IIIb) and (VII) are commercially available, known from the literature or can be prepared in analogy to processes known from the literature.

The process of the invention can be illustrated by way of example by the following formula scheme:

Scheme

Further processes for preparing pyrazolo[3,4-d]pyrimidin-4-ones are known and can likewise be employed to synthesize the compounds of the invention (see, for example: P. Schmidt et al., *Helvetica Chimica Acta* 1962, 189, 1620ff.).

The compounds of the invention show a valuable range of pharmacological and pharmacokinetic effects which could not have been predicted.

They are therefore suitable for use as medicaments for the treatment and/or prophylaxis of diseases in humans and animals.

For the purposes of the present invention, the term "treatment" includes prophylaxis.

It has surprisingly been found that selective PDE9A inhibitors are suitable for producing medicaments for improving perception, concentration, learning or memory.

The compounds of the invention can, by reason of their pharmacological and pharmacokinetic properties, be employed alone or in combination with other medicaments for improving perception, concentration, learning and/or memory.

A PDE9A inhibitor for the purposes of the invention is a compound which inhibits human PDE9A under the conditions indicated below with an $IC_{50}$ of less than 10 μM, preferably less than 1 μM.

A selective PDE9A inhibitor for the purposes of the invention is a compound which inhibits human PDE9A under the conditions indicated below more strongly than human PDE1C, PDE2A, PDE3B, PDE4B, PDE5A, PDE7B, PDE8A, PDE10A and PDE11. A preferred $IC_{50}$ (PDE9A)/$IC_{50}$ (PDE1C, PDE2A, PDE3B, PDE4B, PDE5A, PDE7B and PDE10A) ratio is less than 0.2.

The selective PDE9A inhibitors are particularly suitable for improving perception, concentration, learning or memory after cognitive impairments like those occurring in particular in situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia with dementia or Korsakoff's psychosis.

The in vitro effect of the compounds of the invention can be shown with the following biological assays:

PDE Inhibition

Recombinant PDE1C (GenBank/EMBL Accession Number: NM_005020, Loughney et al. *J. Biol. Chem.* 1996 271, 796-806), PDE2A (GenBank/EMBL Accession Number: NM_002599, Rosman et al. *Gene* 1997 191, 89-95), PDE3B (GenBank/EMBL Accession Number: NM_000922, Miki et al. *Genomics* 1996, 36, 476-485), PDE4B (GenBank/EMBL Accession Number: NM_002600, Obernolte et al. *Gene.* 1993, 129, 239-247), PDE5A (GenBank/EMBL Accession Number: NM_001083, Loughney et al. *Gene* 1998, 216, 139-147), PDE7B (GenBank/EMBL Accession Number: NM_018945, Hetman et al. *Proc. Natl. Acad. Sci. U.S.A.* 2000, 97, 472-476), PDE8A (GenBank/EMBL Accession Number: AF_056490, Fisher et al. *Biochem. Biophys. Res. Commun.* 1998 246, 570-577), PDE9A (Fisher et al., J. Biol. Chem, 1998, 273 (25): 15559-15564), PDE10A (GenBank/EMBL Accession Number: NM_06661, Fujishige et al. *J Biol Chem.* 1999, 274, 18438-45), PDE11A (GenBank/EMBL Accession Number: NM_016953, Fawcett et al. *Proc. Natl. Acad. Sci.* 2000, 97, 3702-3707) were expressed in Sf9 cells with the aid of the pFASTBAC baculovirus expression system (GibcoBRL).

The test substances are dissolved in 100% DMSO and serially diluted to determine their in vitro effect on PDE 9A. Typically, serial dilutions from 200 µM to 1.6 µM are prepared (resulting final concentrations in the assay: 4 µM to 0.032 µM). 2 µL portions of the diluted substance solutions are introduced into the wells of microtiter plates (Isoplate; Wallac Inc., Atlanta, Ga.). Then 50 µL of a dilution of the PDE9A preparation described above are added. The dilution of the PDE9A preparation is chosen so that less than 70% of the substrate is converted during the subsequent incubation (typical dilution: 1:10000; dilution buffer: 50 mM Tris/HCl pH 7.5, 8.3 mM $MgCl_2$, 1.7 mM EDTA, 0.2% BSA). The substrate, [8-$^3$H] guanosine 3',5'-cyclic phosphate (1 µCi/µL; Amersham Pharmacia Biotech., Piscataway, N.J.) is diluted 1:2000 with assay buffer (50 mM Tris/HCl pH 7.5, 8.3 mM $MgCl_2$, 1.7 mM EDTA) to a concentration of 0.0005 µCi/µL. The enzyme reaction is finally started by adding 50 µL (0.025 µCi) of the diluted substrate. The assay mixtures are incubated at room temperature for 60 min and the reaction is stopped by adding 25 µl of a PDE9A inhibitor (e.g. the inhibitor from preparation example 1, final concentration 10 µM) dissolved in assay buffer. Immediately thereafter, 25 µL of a suspension containing 18 mg/mL Yttrium Scintillation Proximity Beads (Amersham Pharmacia Biotech., Piscataway, N.J.) are added. The microtiter plates are sealed with a film and left to stand at room temperature for 60 min. The plates are then measured for 30 s per well in a Microbeta scintillation counter (Wallac Inc., Atlanta, Ga.). $IC_{50}$ values are determined from the graphical plot of the substance concentration versus the percentage inhibition.

The in vitro effect of test substances on recombinant PDE3B, PDE4B, PDE7B, PDE8A, PDE10A and PDE11A is determined in accordance with the assay protocol described above for PDE 9A with the following adaptations: [5',8-$^3$H] adenosine 3',5'-cyclic phosphate (1 µCi/µL; Amersham Pharmacia Biotech., Piscataway, N.J.) is used as substrate. Addition of an inhibitor solution to stop the reaction is unnecessary. Instead, the incubation of substrate and PDE is followed immediately by addition of the yttrium scintillation proximity beads as described above and thus the reaction is stopped. To determine a corresponding effect on recombinant PDE1C, PDE2A and PDE5A, the protocol is additionally adapted as follows: with PDE1C, additionally $10^{-7}$ M calmodulin and 3 mM $CaCl_2$ are added to the reaction mixture. PDE2A is stimulated in the assay by adding 1 µM cGMP and is assayed with a BSA concentration of 0.01%. The substrate employed for PDE1C and PDE2A is [5',8-$^3$H] adenosine 3',5'-cyclic phosphate (1 µCi/µL; Amersham Pharmacia Biotech., Piscataway, N.J.), and for PDE5A is [8-$^3$H] guanosine 3',5'-cyclic phosphate (1 µCi/µL; Amersham Pharmacia Biotech., Piscataway, N.J.).

The PDE9A-inhibiting effect of the compounds of the invention can be shown by means of the following examples:

TABLE 1

| Example | $IC_{50}$ [nM] |
|---|---|
| 1 | 20 |
| 2 | 30 |
| 4 | 30 |
| 10 | 64 |
| 13 | 30 |

Increasing the Intracellular Neuronal cGMP Concentration in Cell Cultures

PDE9A inhibitors increase the intracellular neuronal cGMP in cultivated primary cortical neurons.

Rat embryos (embryonic day E17-E19) were decapitated, and the heads were transferred into dissection dishes filled with dissection medium (DMEM, penicillin/streptomycin; both from Gibco). The scalp and roof of the skull were removed, and the exposed brains were transferred into another Petri dish with dissection medium. Using a binocular microscope and two forceps, the cerebrum (cortex) was isolated and cooled to 4° C. using ice. This dissection and the isolation of the cortical neurons were then carried out in accordance with a standard protocol using the papain kit (Worthington Biochemical Corporation, Lakewood, N.J. 08701, USA) (Huettner et al. *J. Neurosci.* 1986, 6, 3044-3060). The mechanically isolated cortical neurons were cultivated at 150 000 cells/well in 200 µl Neurobasal medium/well (Neurobasal; B27 Supplement; 2 mM L-glutamine; in the presence of penicillin/streptomycin; all agents from Gibco) in 96-well plates (pretreated with poly-D-lysine 100 µg/ml for 30 min) under standard conditions (37° C., 5% $CO_2$) for 7 days. After 7 days, the medium was removed and the cells were washed with HBSS buffer (Hank's balanced salt solution, Gibco/BRL). Then 100 µl of the compound of the invention, dissolved in HBSS buffer (previously dissolved in 100% DMSO: 10 mM), are put on the cells. A further 100 µl of HBSS buffer are then added, so that the final concentration of the compounds of the invention is for example in a range from 20 nM to 10 µM, and incubated at 37° C. for 20 min. The assay buffer is then completely removed. The cells are then lyzed in 200 µl of lysis buffer (cGMP Kit code RPN 226; from Amersham Pharmacia Biotech.) and the cGMP concentration is measured as stated by the manufacturer. All measurements are carried out in triplicates. The statistical analysis takes place using Prism Software version 2.0 (GraphPad Software Inc., San Diego, Calif. USA).

Incubation of the primary neurons with the compounds of the invention led to an increase in the cGMP content.

Long-Term Potentiation

Long-term potentiation is regarded as a cellular correlate of learning and memory processes. The following method can be used to determine whether PDE9 inhibition has an influence on long-term potentiation:

Rat hippocampi are placed at an angle of about 70 degrees to the cutting blade (chopper). 400 μm-thick slices of the hippocampus are prepared. The slices are removed from the blade using a very soft, thoroughly wetted brush (marten hair) and transferred into a glass vessel with cold nutrient solution (124 mM NaCl, 4.9 mM KCl, 1.3 mM $MgSO_4 \times 7\ H_2O$, 2.5 mM $CaCl_2$ anhydrous, 1.2 mM $KH_2PO_4$, 25.6 mM $NaHCO_3$, 10 mM glucose, pH 7.4) gassed with 95% $O_2$/5% $CO_2$. During the measurement, the slices are kept in a temperature-controlled chamber under a 1-3 mm-high liquid level. The flow rate is 2.5 ml/min. The preliminary gassing takes place under a slightly elevated pressure (about 1 atm) and through a microneedle in the prechamber. The slice chamber is connected to the prechamber in such a way that a minicirculation can be maintained. The minicirculation is driven by the 95% $O_2$/5% $CO_2$ flowing out through the microneedle. The freshly prepared hippocampus slices are adapted in the slice chamber at 33° C. for at least 1 hour.

The stimulus level is chosen so that the focal excitatory postsynaptic potentials (fEPSP) are 30% of the maximum excitatory postsynaptic potential (EPSP). A monopolar stimulation electrode consisting of lacquered stainless steel, and a constant-current biphasic stimulus generator (AM Systems 2100) are used for local stimulation of the Schaffer collaterals (voltage: 1-5 V, pulse width of one polarity 0.1 ms, total pulse 0.2 ms). Glass electrodes (borosilicate glass with filament, 1-5 MOhm, diameter: 1.5 mm, tip diameter: 3-20 μm), filled with normal nutrient solution, are used to record the excitatory postsynaptic potentials (fEPSP) from the stratum radiatum. The field potentials are measured versus a chlorinated silver reference electrode located at the edge of the slice chamber using a DC voltage amplifier. The field potentials are filtered through a low-pass filter (5 kHz). The slope of the fEPSPs (fEPSP slope) is determined for the statistical analysis of the experiments. The recording, analysis and control of the experiment takes place with the aid of a software program (PWIN) which was developed in the Department of Neurophysiology. The formation of the average fEPSP slopes at the respective time points and construction of the diagrams takes place with the aid of the EXCEL software, with automatic data recording by an appropriate macro.

Superfusion of the hippocampus slices with a 10 μM solution of the compounds of the invention leads to a significant increase in the LTP.

Social Recognition Test

The social recognition test is a learning and memory test. It measures the ability of rats to distinguish between known and unknown members of the same species. This test is therefore suitable for examining the learning- or memory-improving effect of the compounds of the invention.

Adult rats housed in groups are placed singly in test cages 30 min before the start of the test. Four min before the start of the test, the test animal is put in an observation box. After this adaptation time, a juvenile animal is put in with the test animal and the absolute time for which the adult animal inspects the young one is measured for 2 min (trial 1). All behaviors clearly directed at the young animal are measured, i.e. anogenital inspection, pursuit and grooming, during which the old animal was no further than 1 cm from the young animal. The juvenile is then removed, and the adult is treated with a compound of the invention or vehicle and subsequently returned to its own cage. The test is repeated after a retention time of 24 hours (trial 2). A diminished social interaction time compared with trial 1 indicates that the adult rat remembers the young animal.

The adult animals receive intraperitoneal injections directly following trial 1 either with vehicle (10% ethanol, 20% Solutol, 70% physiological saline) or 0.1 mg/kg, 0.3 mg/kg, 1.0 mg/kg or 3.0 mg/kg compound of the invention dissolved in 10% ethanol, 20% Solutol, 70% physiological saline. Vehicle-treated rats show no reduction in the social interaction time in trial 2 compared with trial 1. They have consequently forgotten that they have already had contact with the young animal. Surprisingly, the social interaction time in the second run after treatment with the compounds of the invention is significantly reduced compared with those treated with vehicle. This means that the substance-treated rats have remembered the juvenile animal and thus the compounds of the invention display an improving effect on learning and memory.

The present invention further relates to a method for the treatment and/or prophylaxis of disorders, in particular of the aforementioned disorders, using an effective amount of the compounds of the invention.

The present invention further relates to medicaments comprising at least one compound of the invention and one or more other active ingredients, in particular for the treatment and/or prophylaxis of the aforementioned disorders.

The compounds of the invention may have systemic and/or local effects. They can for this purpose be administered in a suitable way, such as, for example, by the oral, parenteral, pulmonary, nasal, sublingual, lingual, buccal, rectal, dermal, transdermal, conjunctival or otic route or as implant or stent.

The compounds of the invention can be administered in suitable administration forms for these administration routes.

Administration forms suitable for oral administration are those which function according to the state of the art and deliver the compounds of the invention in a rapid and/or modified way, and which contain the compounds of the invention in crystalline and/or amorphized and/or dissolved form, such as, for example, tablets (uncoated or coated tablets, for example with coatings which are resistant to gastric juice or dissolve slowly or are insoluble and which control the release of the compound of the invention), tablets which rapidly disintegrate in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, injection and infusion preparations in the form of solutions, suspensions, emulsions, lyophilisates or sterile powders.

Examples suitable for other administration routes are medicinal forms for inhalation (inter alia powder inhalators, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking tastes and/or odors.

The present invention further relates to medicaments which comprise at least one compound of the invention, normally together with one or more inert, non-toxic, pharmaceutically suitable excipients, and to the use thereof for the aforementioned purposes.

It has generally proved advantageous on parenteral administration to administer amounts of about 0.001 to 10 mg/kg of body weight per day to achieve effective results. The amount per day on oral administration is about 0.005 to 3 mg/kg of body weight.

It may nevertheless be necessary to deviate from the stated amounts, in particular as a function of body weight, administration route, individual behavior towards the active ingredient, type of preparation and time or interval over which administration takes place. Thus, it may in some cases be sufficient to make do with less than the aforementioned minimum amount, whereas in other cases the stated upper limit must be exceeded. Where larger amounts are administered, it may be advisable to divide them into a plurality of single doses over the day.

The percentage data in the following tests and examples are, unless indicated otherwise, percentages by weight; parts are parts by weight. Solvent ratios, dilution ratios and concentration data for liquid/liquid solutions are in each case based on volume.

ABBREVIATIONS USED

DCI direct chemical ionization (in MS)
DCM dichloromethane
DMSO dimethyl sulfoxide
equiv. equivalent(s)
ESI electrospray ionization (in MS)
HPLC high pressure, high performance liquid chromatography
m.p. melting point
MS mass spectroscopy
NMR nuclear magnetic resonance spectroscopy
TRIS 2-amino-2-(hydroxymethyl)-1,3-propanediol

STARTING COMPOUNDS

Example 1A

5-Amino-1-cyclohexyl-1H-pyrazole-4-carbonitrile

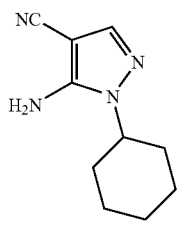

Firstly ethoxymethylenemalononitrile (2.43 g, 19.9 mmol) and then 8 ml of triethylamine are added to a solution of cyclohexylhydrazine hydrochloride (3 g, 19.9 mmol) in 36 ml of ethanol at room temperature. The mixture is refluxed for 20 min and then cooled. The solvent is stripped off in a rotary evaporator, and the residue is taken up in DCM, washed with aqueous sodium bicarbonate solution, dried over sodium sulfate, filtered and concentrated in vacuo. The crude product is chromatographed on silica gel (mobile phase: dichloromethane/methanol 0-10%).

Yield: 1.95 g (51% of theory)

MS (DCI): m/z=191 (M+H)$^+$ $^1$H NMR (200 MHz, DMSO-d$_6$): δ=7.5 (s, 1H), 6.5 (s, 2H), 4.0 (m, 1H), 1.95-1.05 (m, 10H) ppm.

Example 2A

5-Amino-1-cyclopentyl-1H-pyrazole-4-carbonitrile

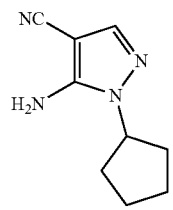

Preparation takes place in analogy to the method for Example 1A.

MS (ESI): m/z=177 (M+H)$^+$ $^1$H NMR (200 MHz, CDCl$_3$): δ=7.5 (s, 1H), 4.45 (br. s, 2H), 4.35 (m, 1H), 2.2-1.55 (m, 6H) ppm.

Example 3A

5-Amino-1-(1-ethylpropyl)-1H-pyrazole-4-carbonitrile

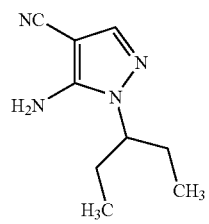

Preparation takes place in analogy to the method for Example 1A.

MS (ESI): m/z=179 (M+H)$^+$ $^1$H NMR (300 MHz, DMSO-d$_6$): δ=7.55 (s, 1H), 6.45 (s, 2H), 4.0 (m, 1H), 1.8-1.55 (m, 4H), 0.65 (t, 6H) ppm.

Example 4A

5-Amino-1-cyclohexyl-1H-pyrazole-4-carboxamide

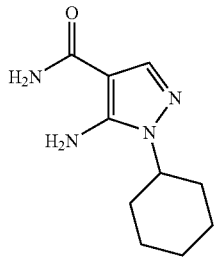

18 ml of 30% strength hydrogen peroxide solution are added to a solution of 5-amino-1-cyclohexyl-1H-pyrazole-4-carbonitrile (1.86 g, 9.81 mmol) in a mixture of 73 ml of ethanol and 90 ml of concentrated aqueous ammonia solution at room temperature, and the mixture is stirred at room temperature for 1 h. The nonaqueous solvents are then stripped off in a rotary evaporator. The product precipitates as solid from the remaining mixture and is filtered off with suction, washed with a little water and dried under high vacuum.

Yield: 1.77 g (86% of theory)
MS (DCI): m/z=209 (M+H)$^+$
$^1$H NMR (300 MHz, DMSO-d$_6$): δ=7.6 (s, 1H), 7.3-6.4 (broad, 2H), 6.1 (s, 2H), 3.95 (m, 1H), 1.95-1.05 (m, 10H) ppm.

Example 5A

5-Amino-1-cyclopentyl-1H-pyrazole-4-carboxamide

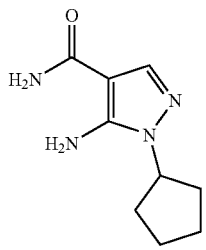

Preparation takes place in analogy to the method for Example 4A.
MS (ESI): m/z=195 (M+H)$^+$
$^1$H NMR (200 MHz, CDCl$_3$): δ=7.5 (s, 1H), 5.6-4.8 (broad, 4H), 4.35 (m, 1H), 2.2-1.55 (m, 8H) ppm.

Example 6A

5-Amino-1-(1-ethylpropyl)-1H-pyrazole-4-carboxamide

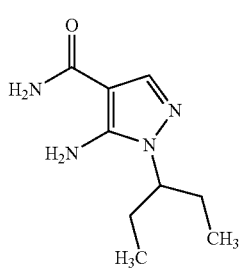

Preparation takes place in analogy to the method for Example 4A.
MS (ESI): m/z=197 (M+H)$^+$
$^1$H NMR (300 MHz, DMSO-d$_6$): δ=7.65 (s, 1H), 6.9 (br. s, 2H), 6.1 (s, 2H), 3.9 (m, 1H), 1.85-1.6 (m, 4H), 0.7 (t, 6H) ppm.

EXEMPLARY EMBODIMENTS

Example 1

6-(3-Chlorobenzyl)-1-cyclopentyl-1,5-dihydro-4H-pyrazolo[3,4-d]pyrimidin-4-one

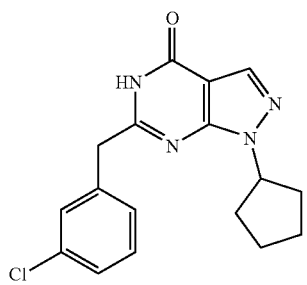

Under argon, 180 mg (0.91 mmol) of 5-amino-1-cyclopentyl-1H-pyrazole-4-carboxamide and 575 mg (2.72 mmol; 3 equiv.) of ethyl (3-chlorophenyl)acetate are introduced into 3.5 ml of absolute ethanol. At 0° C., 127 mg of sodium hydride (60% dispersion in mineral oil; 3.18 mmol; 3.5 equiv.) are slowly added in a countercurrent of argon. The resulting mixture is slowly warmed and stirred under reflux for 18 h. The mixture is worked up by adding 50 ml of water and extracted several times with ethyl acetate. The combined organic phases are dried over sodium sulfate and concentrated in vacuo. The crude product is purified by preparative HPLC.

Yield: 244 mg (81% of theory)
MS (ESI): m/z=329 (M+H)$^+$
m.p.: 159° C.
$^1$H NMR (200 MHz, DMSO-d$_6$): δ=12.3 (s, 1H), 8.0 (s, 1H), 7.5-7.2 (m, 4H), 5.05 (m, 1H), 3.95 (s, 2H), 2.2-1.5 (m, 8H) ppm.

Example 2

6-(2-Fluorobenzyl)-1-cyclopentyl-1,5-dihydro-4H-pyrazolo[3,4-d]pyrimidin-4-one

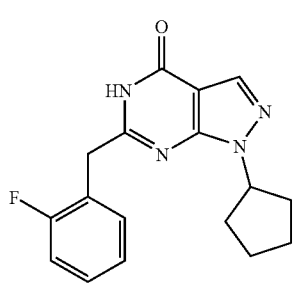

The product is obtained in analogy to Example 1 starting from 100 mg (0.5 mmol) of 5-amino-1-cyclopentyl-1H-pyrazole-4-carboxamide and 260 mg (1.51 mmol) of methyl (2-fluorophenyl)acetate.

Yield: 100 mg (63% of theory)
MS (DCI): m/z=313 (M+H)⁺
m.p.: 180° C.
¹H NMR (400 MHz, DMSO-$d_6$): δ=12.25 (s, 1H), 8.0 (s, 1H), 7.4-7.3 (m, 2H), 7.2-7.1 (m, 2H), 4.95 (m, 1H), 4.05 (s, 2H), 2.05-1.55 (m, 8H) ppm.

Example 3

6-(3-Bromobenzyl)-1-cyclopentyl-1,5-dihydro-4H-pyrazolo[3,4-d]pyrimidin-4-one

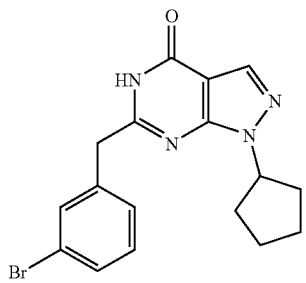

The product is obtained in analogy to Example 1 starting from 80 mg (0.4 mmol) of 5-amino-1-cyclopentyl-1H-pyrazole-4-carboxamide and 277 mg (1.21 mmol) of methyl (3-bromophenyl)acetate.

Yield: 93 mg (62% of theory)
MS (ESI): m/z=373 (M+H)⁺
m.p.: 159° C.
¹H NMR (400 MHz, DMSO-$d_6$): δ=12.2 (s, 1H), 8.0 (s, 1H), 7.6 (s, 1H), 7.5-7.35 (m, 3H), 5.05 (m, 1H), 4.0 (s, 2H), 2.1-1.6 (m, 8H) ppm.

Example 4

6-(3,4-Dichlorobenzyl)-1-cyclopentyl-1,5-dihydro-4H-pyrazolo[3,4-d]pyrimidin-4-one

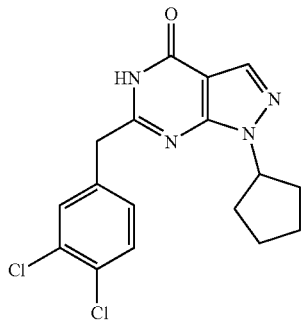

The product is obtained in analogy to Example 1 starting from 75 mg (0.38 mmol) of 5-amino-1-cyclopentyl-1H-pyrazole-4-carboxamide and 254 mg (1.14 mmol) of methyl (3,4-dichlorophenyl)acetate.

Yield: 94 mg (68% of theory)
MS (ESI): m/z=363 (M+H)⁺
m.p.: 198° C.
¹H NMR (400 MHz, DMSO-$d_6$): δ=12.2 (s, 1H), 8.0 (s, 1H), 7.65 (d, 1H, J=1 Hz), 7.55 (d, 1H, J=7.5 Hz), 7.3 (dd, 1H, J=7.5 Hz, 1 Hz), 5.05 (m, 1H), 4.0 (s, 2H), 2.1-1.6 (m, 8H) ppm.

Example 5

6-(3,5-Dichlorobenzyl)-1-cyclopentyl-1,5-dihydro-4H-pyrazolo[3,4-d]pyrimidin-4-one

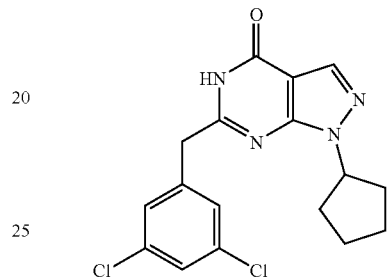

The product is obtained in analogy to Example 1 starting from 150 mg (0.76 mmol) of 5-amino-1-cyclopentyl-1H-pyrazole-4-carboxamide and 507 mg (2.27 mmol) of methyl (3,5-dichlorophenyl)acetate.

Yield: 159 mg (58% of theory)
MS (ESI): m/z=363 (M+H)⁺
m.p.: 177° C.
¹H NMR (200 MHz, DMSO-$d_6$): δ=12.25 (s, 1H), 8.0 (s, 1H), 7.55 (t, 1H, J=1 Hz), 7.45 (d, 2H, J=1 Hz), 5.05 (m, 1H), 4.0 (s, 2H), 2.2-1.5 (m, 8H) ppm.

Example 6

6-(2,3-Dichlorobenzyl)-1-cyclopentyl-1,5-dihydro-4H-pyrazolo[3,4-d]pyrimidin-4-one

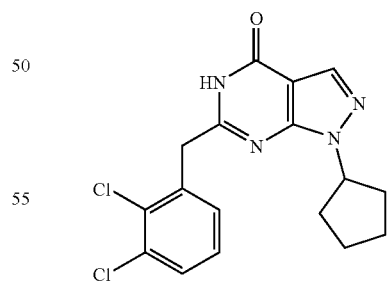

The product is obtained in analogy to Example 1 starting from 150 mg (0.76 mmol) of 5-amino-1-cyclopentyl-1H-pyrazole-4-carboxamide and 406 mg (1.82 mmol) of methyl (2,3-dichlorophenyl)acetate.

Yield: 114 mg (41% of theory)
MS (ESI): m/z=363 (M+H)⁺
m.p.: 181° C.

$^1$H NMR (200 MHz, DMSO-d$_6$): δ=12.35 (s, 1H), 8.0 (s, 1H), 7.6 (m, 1H), 7.4-7.3 (m, 2H), 4.9 (m, 1H), 4.2 (s, 2H), 2.1-1.5 (m, 8H) ppm.

Example 7

6-(3-Chlorobenzyl)-1-(1-ethylpropyl)-1,5-dihydro-4H-pyrazolo[3,4-d]pyrimidin-4-one

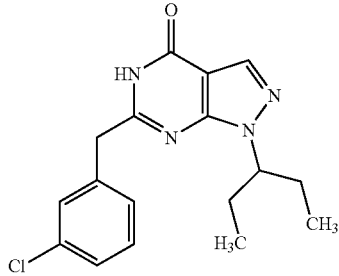

The product is obtained in analogy to Example 1 starting from 150 mg (0.76 mmol) of 5-amino-1-(1-ethylpropyl)-1H-pyrazole-4-carboxamide and 484 mg (2.29 mmol) of ethyl (3-chlorophenyl)acetate.

Yield: 210 mg (83% of theory)

MS (ESI): m/z=331 (M+H)$^+$ m.p.: 138° C.

$^1$H NMR (200 MHz, DMSO-d$_6$): δ=12.3 (s, 1H), 8.0 (s, 1H), 7.45-7.25 (m, 4H), 4.45 (m, 1H), 4.0 (s, 2H), 2.0-1.7 (m, 4H), 0.6 (t, 6H, J=7.5 Hz) ppm.

Example 8

6-(3-Methylbenzyl)-1-cyclopentyl-1,5-dihydro-4H-pyrazolo[3,4-d]pyrimidin-4-one

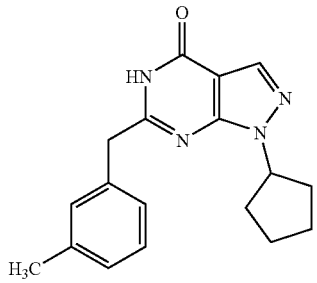

The product is obtained in analogy to Example 1 starting from 200 mg (1.01 mmol) of 5-amino-1-cyclopentyl-1H-pyrazole-4-carboxamide and 550 mg (3.03 mmol) of ethyl (3-methylphenyl)acetate.

Yield: 222 mg (71% of theory)

MS (ESI): m/z=309 (M+H)$^+$ m.p.: 152° C.

$^1$H NMR (200 MHz, DMSO-d$_6$): δ=12.2 (s, 1H), 8.0 (s, 1H), 7.3-7.0 (m, 4H), 5.1 (m, 1H), 3.95 (s, 2H), 2.3 (s, 3H), 2.2-1.55 (m, 8H) ppm.

Example 9

6-(2,5-Dichlorobenzyl)-1-(1-ethylpropyl)-1,5-dihydro-4H-pyrazolo[3,4-d]pyrimidin-4-one

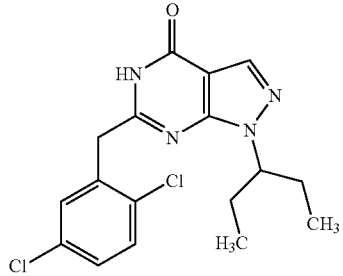

The product is obtained in analogy to Example 1 starting from 200 mg (1.0 mmol) of 5-amino-1-(1-ethylpropyl)-1H-pyrazole-4-carboxamide and 806 mg (3.5 mmol) of methyl (2,5-dichlorophenyl)acetate.

Yield: 51 mg (14% of theory)

MS (ESI): m/z=365 (M+H)$^+$ m.p.: 134° C.

$^1$H NMR (300 MHz, DMSO-d$_6$): δ=12.3 (s, 1H), 8.0 (s, 1H), 7.55-7.35 (m, 3H), 4.2 (m, 1H), 4.15 (s, 2H), 1.9-1.65 (m, 4H), 0.55 (t, 6H, J=7.5 Hz) ppm.

Example 10

6-(3-Methylbenzyl)-1-(1-ethylpropyl)-1,5-dihydro-4H-pyrazolo[3,4-d]pyrimidin-4-one

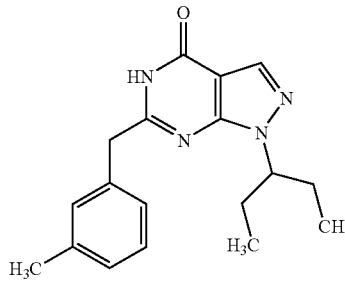

The product is obtained in analogy in Example 1 starting from 200 mg (1.0 mmol) of 5-amino-1-(1-ethylpropyl)-1H-pyrazole-4-carboxamide and 534 mg (3.0 mmol) of ethyl (3-methylphenyl)acetate.

Yield: 187 mg (60% of theory)

MS (ESI): m/z=311 (M+H)$^+$ m.p.: 128° C.

¹H NMR (200 MHz, DMSO-d₆): δ=12.25 (s, 1H), 8.0 (s, 1H), 7.25-7.0 (m, 4H), 4.5 (m, 1H), 3.95 (s, 2H), 2.25 (s, 3H), 2.0-1.7 (m, 4H), 0.6 (t, 6H, J=7.5 Hz) ppm.

Example 11

1-(1-Ethylpropyl)-6-[3-(trifluoromethyl)benzyl]-1,5-dihydro-4H-pyrazolo[3,4-d]-pyrimidin-4-one

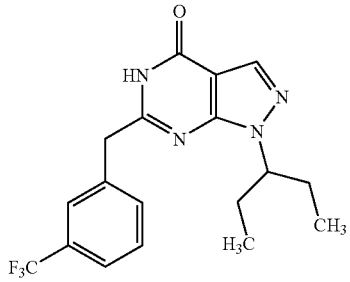

The product is obtained in analogy to Example 1 starting from 150 mg (0.75 mmol) of 5-amino-1-(1-ethylpropyl)-1H-pyrazole-4-carboxamide and 490 mg (2.25 mmol) of methyl (3-trifluoromethylphenyl)acetate.

Yield: 159 mg (58% of theory)
MS (ESI): m/z=365 (M+H)⁺
m.p.: 120° C.
¹H NMR (400 MHz, DMSO-d₆): δ=12.3 (s, 1H), 8.0 (s, 1H), 7.7 (s, 1H), 7.7-7.5 (m, 3H), 4.4 (m, 1H), 4.1 (s, 2H), 1.95-1.75 (m, 4H), 0.6 (t, 6H, J=7.5 Hz) ppm.

Example 12

1-Cyclopentyl-6-(3-nitrobenzyl)-1,5-dihydro-4H-pyrazolo[3,4-d]pyrimidin-4-one

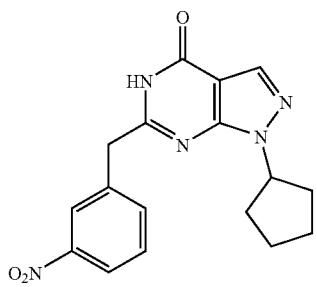

The product is obtained in analogy to Example 1 starting from 668 mg (3.44 mmol) of 5-amino-1-cyclopentyl-1H-pyrazole-4-carboxamide and 3.5 g (13.7 mmol) of ethyl 3-nitrophenylacetate.

Yield: 10 mg (1% of theory)
MS (ESI): m/z=340 (M+H)⁺

¹H NMR (300 MHz, DMSO-d₆): δ=12.3 (s, 1H), 8.3 (s, 1H), 8.15 (m, 1H), 8.0 (s, 1H), 7.8 (d, 1H, J=8 Hz), 7.6 (t, 1H, J=8 Hz), 5.0 (m, 1H), 4.15 (s, 2H), 2.1-1.6 (m, 8H).

Example 13

6-(3-Chlorobenzyl)-1-cyclopentyl-1,5-dihydro-4H-pyrazolo[3,4-d]pyrimidine-4-thione

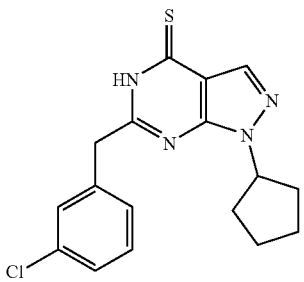

50 mg (0.23 mmol, 1.5 equiv.) of diphosphorus pentasulfide are added to a solution of 50 mg (0.15 mmol) of 6-(3-chlorobenzyl)-1-cyclopentyl-1,5-dihydro-4H-pyrazolo[3,4-d]pyrimidin-4-one (Example 1) in 1 ml of pyridine at room temperature, and the mixture is then stirred under reflux overnight. After cooling, the reaction solution is mixed with 10 ml of ice-cold 2.5% strength sodium bicarbonate solution and extracted three times with ethyl acetate. The combined organic phases are washed with saturated brine, dried over sodium sulfate and concentrated in vacuo. The crude product is purified by preparative HPLC.

Yield: 36 mg (68% of theory)
MS (ESI): m/z=345 (M+H)⁺
m.p.: 154° C.
¹H NMR (300 MHz, DMSO-d₆): δ=13.6 (s, 1H), 8.15 (s, 1H), 7.5 (s, 1H), 7.4-7.25 (m, 3H), 5.05 (m, 1H), 4.1 (s, 2H), 2.1-1.6 (m, 8H).

Example 14

1-Cyclopentyl-6-[2-(trifluoromethoxy)benzyl]-1,5-dihydro-4H-pyrazolo[3,4-d]-pyrimidin-4-one

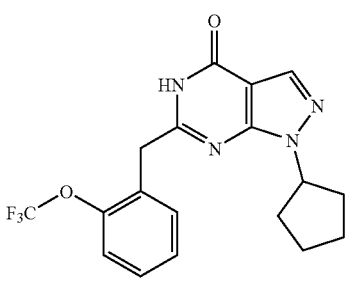

The product is obtained in analogy to Example 1 starting from 50 mg (0.26 mmol) of 5-amino-1-cyclopentyl-1H-pyrazole-4-carboxamide and 301 mg (1.29 mmol) of methyl [2-(trifluoromethoxy)phenyl]acetate.

Yield: 64 mg (63% of theory)
MS (DCI): m/z=379 (M+H)⁺
m.p.: 161° C.

$^1$H NMR (400 MHz, DMSO-d$_6$): δ=12.25 (s, 1H), 8.0 (s, 1H), 7.5-7.3 (m, 4H), 4.9 (m, 1H), 4.1 (s, 2H), 2.05-1.5 (m, 8H) ppm.

The invention claimed is:

1. A compound of the formula

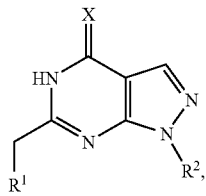
(I)

in which

R$^1$ is phenyl which is substituted by 1 to 5 substituents independently of one another selected from the group of halogen, C$_1$-C$_6$-alkyl, trifluoromethyl, trifluoromethoxy, cyano, hydroxy, nitro and C$_1$-C$_6$-alkoxy, R$^2$ is C$_4$-C$_6$-cycloalkyl, X is oxygen or sulfur, or a salt thereof.

2. A compound as claimed in claim 1, where

R$^1$ is phenyl which is substituted by 1 to 3 substituents independently of one another selected from the group of fluorine, chlorine, bromine, C$_1$-C$_4$-alkyl, trifluoromethyl, trifluoromethoxy, cyano, hydroxy, nitro and C$_1$-C$_4$-alkoxy, R$^2$ is C$_5$-C$_6$-cycloalkyl, X is oxygen or sulfur, or a salt thereof.

3. A compound as claimed in claim 1 of the formula

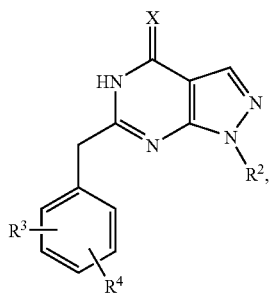
(Ia)

in which

R$^3$ is hydrogen or chlorine,

R$^4$ is fluorine, chlorine, bromine, methyl, trifluoromethyl,

R$^2$ is cyclopentyl,

X is oxygen or sulfur, or a salt thereof.

4. A compound as claimed in claim 1 of the formula (Ia), where

R$^3$ is hydrogen or chlorine,

R$^4$ is fluorine, chlorine, bromine, methyl, trifluoromethyl,

R$^2$ is cyclopentyl,

X is oxygen, or a salt thereof.

5. A process for preparing a compound of the formula (I):

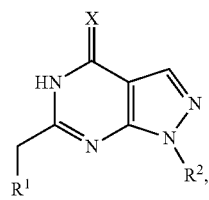
(I)

in which

R$^1$ is phenyl which is substituted by 1 to 5 substituents independently of one another selected from the group of halogen, C$_1$-C$_6$-alkyl, trifluoromethyl, trifluoromethoxy, cyano, hydroxy, nitro and C$_1$-C$_6$-alkoxy, R$^2$ is pentan-3-yl or C$_4$-C$_6$-cycloalkyl, X is oxygen or sulfur, or a salt thereof, wherein

[A] a compound of the formula

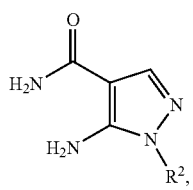
(II)

in which

R$^2$ has the meanings indicated, is converted by reaction with a compound of the formula

R$^1$—CH$_2$—C(O)—Z (IIIa), in which

R$^1$ has the meanings indicated, and

Z is chlorine or bromine, initially in the presence of a base into a compound of the formula

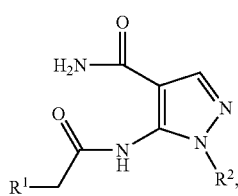
(IV)

in which

R¹ and R² have the meanings indicated, then cyclized in the presence of a base to a compound of the formula

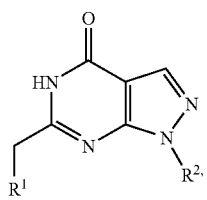

(Ib)

in which

R¹ and R² have the meanings indicated, or

[B] a compound of the formula (II) is reacted with direct cyclization to (Ib) with a compound of the formula R¹—CH₂—C(O)—OR⁵  (IIIb), in which R¹ has the meanings indicated, and R⁵ is methyl or ethyl, in the presence of a base, or

[C] a compound of the formula

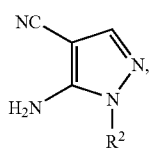

(V)

in which

R² has the meanings indicated, is converted initially by reaction with a compound of the formula (IIIa) in the presence of a base into a compound of the formula

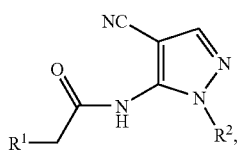

(VI)

in which

R¹ and R² have the meanings indicated, and the latter are cyclized in a second step in the presence of a base and of an oxidizing agent to (Ib), and a compound of the formula (Ib) is then converted where appropriate by reaction with a sulfurizing agent into the thiono derivatives of the formula

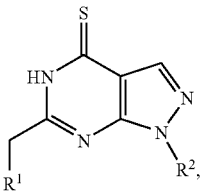

(Ic)

in which

R¹ and R² have the meanings indicated, and the resulting compound of the formula (I) is optionally reacted with the appropriate bases or acids to give a salt thereof.

6. A medicament comprising at least one of the compounds as claimed in any one of claims 1 to 4 and at least one pharmaceutically acceptable, essentially non-toxic carrier or excipient.

7. A method for treating an impairment of learning and/or memory which is a consequence of Alzheimer's disease comprising administering to a human or animal an effective amount of a compound of the formula (I):

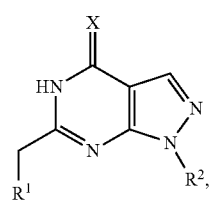

(I)

in which

R¹ is phenyl which is substituted by 1 to 5 substituents independently of one another selected from the group of halogen, $C_1$-$C_6$-alkyl, trifluoromethyl, trifluoromethoxy, cyano, hydroxy, nitro and $C_1$-$C_6$-alkoxy, R² is pentan-3-yl or $C_4$-$C_6$-cycloalkyl, X is oxygen or sulfur, or a salt thereof.

8. The process of claim 5, wherein the sulfurizing agent is diphosphorus pentasulfide.

9. A method for producing a medicament useful for improving perception, concentration, learning and/or memory comprising formulating a compound of formula (I) together with at least one pharmaceutically acceptable excipient:

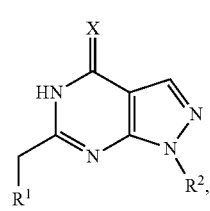

(I)

in which
R¹ is phenyl which is substituted by 1 to 5 substituents independently of one another selected from the group of halogen, $C_1$-$C_6$-alkyl, trifluoromethyl, trifluoromethoxy, cyano, hydroxy, nitro and $C_1$-$C_6$-alkoxy,
R² is $C_4$-$C_6$-cycloalkyl,
X is oxygen or sulfur,
or a salt thereof,
in a form useful for improving perception, concentration, learning and/or memory in a human or animal.

10. A pharmaceutical composition comprising a compound of the formula (I):

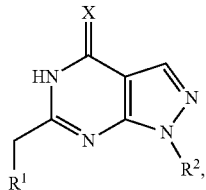

in which

R¹ is phenyl which is substituted by 1 to 5 substituents independently of one another selected from the group of halogen, $C_1$-$C_6$-alkyl, trifluoromethyl, trifluoromethoxy, cyano, hydroxy, nitro and $C_1$-$C_6$-alkoxy, R² is $C_4$-$C_6$-cycloalkyl, X is oxygen or sulfur, or a salt thereof, as the active moiety, together with at least one pharmaceutically acceptable excipient.

* * * * *